United States Patent [19]

Widlanski

[11] Patent Number: 5,714,361
[45] Date of Patent: Feb. 3, 1998

[54] PHOSPHATASE/PHOSPHODIESTERASE ENZYME INHIBITORS AND METHODS

[75] Inventor: Theodore S. Widlanski, Bloomington, Ind.

[73] Assignee: Indiana University Foundation, Bloomington, Ind.

[21] Appl. No.: 194,838

[22] Filed: Feb. 14, 1994

[51] Int. Cl.$^6$ .................. C12N 9/99; C07F 9/02
[52] U.S. Cl. ............................. 435/184; 558/210
[58] Field of Search ................. 435/184; 558/210, 558/206; 562/8, 25; 514/143, 144, 147, 148, 274, 261, 242, 262, 460, 473; 544/220, 265, 319, 264; 549/417, 476

[56] References Cited

U.S. PATENT DOCUMENTS

| | | | |
|---|---|---|---|
| 3,911,122 | 10/1975 | Drabek et al. | 514/147 |
| 4,152,372 | 5/1979 | Large et al. | 558/210 |
| 5,273,969 | 12/1993 | Biller et al. | 514/108 |
| 5,281,523 | 1/1994 | Kovach | 435/184 |
| 5,308,766 | 5/1994 | Dennis et al. | 435/184 |

OTHER PUBLICATIONS

Chem. Abs., vol. 115, No. 153777, issued 1991, Zhang et al (II), "Leaving group dependence and proton inventory studies of the phosphoylation of a cytoplasmic phosphotyrosyl protein phosphates from bovine heart".

Khorana Gobind H., "Some recent developments in the chemistry of phosphate esters of biological interest" pp. 1–12, 1962.

Chem. Abs., vol. 121, No. 102719, issued 1994, Wang et al, "Suicide in activation of human prostatic and phosphatase".

Chem. Abs., vol. 120, No. 318198, issued 1994, Zhang et al (I), "Nature of the rate–determining steps of reaction catalyzed by Yersinia phosphatase".

Chem. Abs., vol. 120, No. 72184, issued 1993, Myers et al., "Mechanism–based inactivation of prostatic acid phosphatase".

Chem. Abs., vol. 116, No. 236024, issued 1992, Wissner et al, "Analogs of platelet activating factor–Mono–and bis–aryl phosphate antagonists".

Lichtenthaler, F. W. Chem. Rev. 1961, 61, 607–649.

Gaydou, E. M.; Llinas, J. R. Org. Magn. Resonance 1974, 6, 23–32.

Gaydou, E. M.; Gilbert, P. Org. Mass Spectrom. 1974, 9, 514–524.

Gaydou, E. M. Bull. Soc. Chim. Fr. 1973, 7–8, 2275–2278.

Jung, M. E.; Blum, R. B. Tetrahedron Letters 1977, 43, 3791–3794.

Sauer, J. C.; Wilson, J. D. C. J. Am. Chem. Soc. 1955, 77, 3793–3795.

Fryzuk, M. D.; Bosnich, B. J. Am. Chem. Soc. 1979, 101, 3043–3049.

Halperin, B. I.; Donahoe, H. B.; Kleinberg, J.; Vanderwerf, C. A. J. Org. Chem. 1952, 17, 623–629.

Niedballa, U; Vorbrüggen, H., J. Org. Chem. 1974, 39, 3654–3660.

Musicki, B.; Widlanski, T.S., J. Org. Chem. 1990, 55, 4231–4233.

Garner, P.; Ramakanth, S., J. Org. Chem. 1988, 53, 1294–1298.

Vorbrüggen, H.; Krolikiewicz, K.; Bennua, B., Chem. Ber. 1981, 114, 1234–1255.

Kuipers, O.P.; Dekker, N.; Verheij, H.M.; de Haas, G.H., Biochem. 1990, 29, 6094–6102.

Ranganathan, R.S.; Jones, G.H.; Moffatt, J.G., J. Org. Chem. 1974, 39, 290–298.

Carretero, J.C.; Demillequand, M.; Ghosez, L., Tetrahedron 1987, 43, 5125–5134.

Musicki, B.; Widlanski, T.S., Tetrahedron Let. 1991, 32, 1267–1270.

Weinreb, S.M.; Demko, D.M.; Lessen, T.A., Tetrahedron Let. 1986, 27, 2099–2102.

Mahoney, W.S.; Brestensky, D.M.; Stryker, J.M., J. Am. Chem. Soc. 1988, 110, 291–293.

*Primary Examiner*—Allen J. Robinson
*Assistant Examiner*—Deborah Lambkin
*Attorney, Agent, or Firm*—Woodard, Emhardt, Naughton, Moriarty & McNett

[57] ABSTRACT

Described are preferred suicide inhibitors of phosphatase or phosphodiesterase enzymes, and methods for preparing halo enol phosphates which can serve as such suicide inhibitors.

18 Claims, 1 Drawing Sheet

5,714,361

1

PHOSPHATASE/PHOSPHODIESTERASE ENZYME INHIBITORS AND METHODS

This invention was made utilizing funds from the National Institutes of Health Grant No. 5RO1 GM47918. The Government has certain rights in the invention.

BACKGROUND

The present invention relates generally to methods and compositions for inhibiting the activity of enzymes, and, more particularly, to suicide substrates and related methods for inhbiting phosphatase or phosphodiesterase enzymes.

As further background, biological processes such as signal transduction, DNA repair, phospholipid metabolism, glucose utilization, the regulation of protein phosphorylation, and many other cellular activities are linked by a common chemical element—the enzyme-catalyzed cleavage of phosphate ester bonds. As such, the modification of the action of enzymes such as phosphatases and phosphodiesterases can be useful both in vivo and in vitro in diagnostics and assays. However, despite the central roles of phosphatase and phosphodiesterase enzymes, very little has been done toward the discovery of effective inhibitors for the enzymes.

In response to this need, the applicant has discovered novel suicide inhibitors (also known as mechanism-based inactivators) for phosphatase and phosphodiesterase enzymes. Such inhibitors are enzyme substrates that undergo an enzyme-catalyzed transformation to give reactive intermediate that, prior to their release, inactivate the enzyme by forming covalent bond to an active site residue.

SUMMARY OF THE INVENTION

One object of the invention is to provide methods for inhibiting phosphatase and phosphodiesterase enzymes which employ mechanism-based inhibitors which can be adapted to inhibit a broad range of enzymes.

Another object of the invention is to provide regioselective syntheses for preparing mechanism-based inhibitors of phosphatase and phosphodiesterase enzymes which provide good yields and which encompass relatively few steps.

These and other objects are provided by preferred embodiments of the invention, one of which provides a process for inhibiting a phosphatase or phosphodiesterase enzyme, comprising contacting the enzyme with a substrate for the enzyme incorporating a group of the formula:

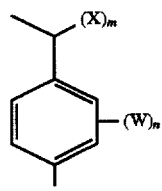

as a phophate ester group.

Another preferred embodiment of the invention provides a suicide inhibitor for a phoshphatase or phosphodiesterase enzyme, comprising a substrate for the enzyme incorporating a group of the formula:

2

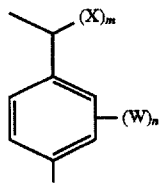

as a phosphate ester group.

Another preferred embodiment of the invention provides a process for inhibiting a phosphatase or phosphodiesterase enzyme, comprising contacting the enzyme with a substrate for the enzyme incorporating a group of the formula IV or V as an enol phosphate:

Another preferred embodiment of the invention provides a suicide inhibitor for a phosphatase or phosphodiesterase enzyme, comprising a substrate for the enzyme incorporating a group of the formula IV or V:

Still another preferred embodiment of the invention provides a method for regioselective synthesis of an enol phosphate compound, comprising reacting a compound of the formula XII

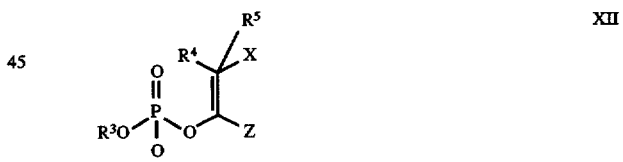

wherein X is halogen and Z is a halogen or an acyl leaving group, $R^3$ is —H or a specificity element, and $R^4$ and $R^5$, which may be the same or may differ from one another, are —H or an organic group having up to about 20 carbon atoms, in the presence of a metal amide base so as to produce an enol phosphate compound of formula XIII

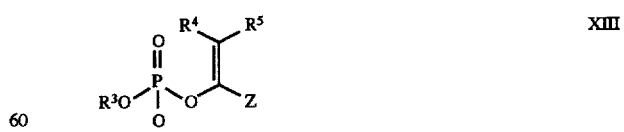

wherein Z, $R^3$, $R^4$ and $R^5$ are as defined above.

Additional embodiments, objects and advantages of the invention will be apparent from the following description.

DESCRIPTION OF THE PREFERRED EMBODIMENT

Figure 1:
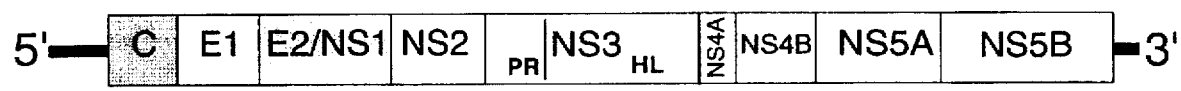
FIG. 1 shows the inactivation of prostatic acid phosphatase with FMPP, and the corresponding phosphonate analogue (see XXI in Experimental, infra.). Reactions were performed by incubating 1 or 9 with PAP (2 μg/mL) in 100 mM sodium acetate buffer pH 5.0 at 25° C. Residual PAP activity was determined by removing 20 μL aliquots and adding them to a 1 mL solution of 3.0 mM p-nitrophenyl phosphate (PNPP) in 100 mM sodium acetate buffer pH 5.0. After 5 minutes in PNPP, the reactions were quenched with 100 μL of 1.25N NaOH. p-Nitrophenoxide concentration was quantitated from the absorbance at 405 nm, using an extinction coefficient of 18,000 M-1 cm-1. (A) Residual PAP activity after incubation with varying concentrations of 1; 5.0 mM (filled circles), 500 μM (open squares), 125 μM (open triangles), 70 μM (filled diamonds), and 50 μM (open circles). (B) Residual PAP activity after treatment with 6.6 mM FMPP (open triangles), or 23 mM of the phosphonate (15 X $K_i$) (closed circles). Note that due to the high concentration of XXI, some residual competitive inhibition is observed.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention relates.

It is well known that phosphatase and phosphodiesterase enzymes are involved in a number of cellular processes such as signal transduction, nucleic acid repair and synthesis, phospholipid metabolism, energy storage and utilization (e.g. glucose storage and utilization), and the regulation of protein phosphorylation.

Because the cleavage of phosphate ester bonds is central to so many cellular activities, the inhibition of the ability of the enzymes involved—e.g. phosphatases and phosphodiesterases—to successfully catalyze such cleavage has taken on a variety of utilities. For example, enzyme inhibition is central to many diagnostic procedures which measure enzyme levels as markers of biological disorders, e.g. in the case of prostatic acid phosphatase, this enzyme is a diagnostic marker for prostate cancer. Antitumor agents rely upon the inhibition of enzymes such as phospholipase C, phospholipase D and PA phosphohydrolase, which catalyze phospholipid hydrolysis and are involved in second messenger release and simulation and control of signaling pathways. Therapeautic compounds for asthma rely upon the inhibition of c-AMP hydrolyis and c-GMP hydrolysis by inhibition of the respective enzymes c-AMP phosphodiesterase and c-GMP phosphodiesterase and concommitant interference with second messenger control. In further utilities, immunosuppressive activity is achieved by inhibition of Calcineurin (phosphoserine/threonine phosphatase), which is involved in phosphoserine hydrolysis. The regulation of glucose levels (e.g. in the control of diabetes) can be achieved by inhibition of the enzyme glucose-6-phosphatase, which catalyzes glucose 6-phosphate hydrolysis and is involved in the release of glucose from the liver. Ribonuclease A (a phosphodiesterase) is currently being widely used in RNA digestion kits. Termination of Ribonuclease A activity at the desired time is critical to such digestions, and suicide substrates for Ribonuclease A can be used to achieve such termination. Additionally, inhibition of phosphotyrosine phosphatase can be used in the regulation of cell growth, see e.g. U.S. Pat. No. 5,155,031. Accordingly, the suicide substrates and related methods of the present invention will find use inter alia in diagnostic procedures, cell growth regulation, and as therapeutic agents.

In accordance with one embodiment of the invention there are provided methods for inhibiting phosphatase enzymes utilizing suicide inhibitors encompassed by formula I:

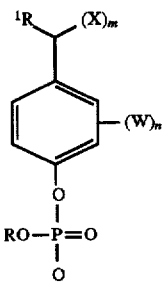

wherein

X is a leaving group, and m is an integer from 1 to 3;

R is —H, or a nucleoside or polynucleotide (usually having up to about 20 nucleotides) attached at the 3'- or 5'- position;

when R is —H, $R^1$ is —H or a specificity element (providing phosphatase inhibitors), and when R is a nucleoside or polynucleotide, $R^1$ is —H or an organic group of up to about 20 carbon atoms (providing phosphodiesterase inhibitors);

n=an integer from 0 to 4; and

W is lower alkyl (i.e. $C_1$ to $C_5$) or an electron-withdrawing group.

"Specificity element", as used herein, means a chemical group which either alone or in combination with other structural elements of the suicide inhibitor, causes the suicide inhibitor to be a substrate for the phosphatase or phosphodiesterase enzyme to be inhibited. It is apparent from the above discussions that there are a great number of known phosphatase and phosphodiesterase enzymes. Likewise, the naturally-occurring substrates for these enzymes are known, and the specificity elements employed in the present invention will correspond to the specificity elements of these naturally-occurring substrates. Thus, generally speaking, the suicide inhibitors of the present embodiment of the invention can be constructed by incorporating the radical

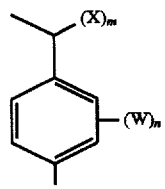

as a phosphoester group in a substrate for a phosphatase or phosphodiesterase enzyme.

With the foregoing in mind, representative specificity elements $R^1$ will include aliphatic, aromatic, or combined aliphatic-aromatic groups, generally having up to about 20 carbon atoms and optionally containing halogen (especially fluorine), sulfur, oxygen or nitrogen atoms. Groups $R^2$ thus include, for example, aliphatic groups which correspond to those occurring on phenyl-containing amino acids such as tyrosine, e.g. where R is —HC($NH_3$)-COO⁻.

The leaving group X will be a group with sufficient leaving capacity to enable the inactivation of the target enzyme by covalent bonding within the active site of the enzyme. Suitable leaving groups include halogens (i.e. iodine, bromine, chlorine and fluorine) and acyl groups —COR² wherein R² is an organic group having up to about 20 carbon atoms. The particular organic group R² is not critical so long as the acyl group remains an effective leaving group. Phenyl groups or $C_1$ to $C_{10}$ aliphatic groups (e.g. alkyl) optionally substituted with phenyl are conveniently employed as R² and are thus preferred.

The phenyl group of the suicide inhibitor of formula I can also be substituted with up to four lower alkyl and/or electron-withdrawing groups W. In particular, it has been found that positioning an electron-withdrawing group at a position ortho to the phosphate group improves the leaving capacity of the group X and can thus provide more potent suicide inhibitors. Suitable electron-withdrawing groups for these purposes include, for example, nitro ($NO_2$), cyano (—CN), sulfonate (—$SO_3H$), and carboxyl (—COOH).

Suicide inhibitors of formula I are preferred for use with enzymes having specificity for aryl substrates, which include, for example, phosphatases such as prostatic acid phosphatase, calcineurin, YOP 51, LAR, and CD45, and phosphodiesterases such as ribonucleosides A and $T_1$.

The synthesis of suicide inhibitors of formula I is straightforward and can be accomplished using conventional procedures and reagents. For example, to synthesise the suicide inhibitor 4-(fluoromethyl)phenyl phosphate, parahydroxybenzaldehyde, HO-Phenyl-CHO, was first phosphorylated with diethylchlorophosphate to form the corresponding diethylphosphate, $(OEt)_2PO$-O-Phenyl-CHO. The diethylphosphate was reduced with sodium borohydride to form the corresponding alcohol, $(OEt)_2PO$-O-Phenyl-$CH_2OH$. The alcohol was converted to the corresponding fluoryl compound, $(OEt)_2PO$-O-Phenyl-$CH_2F$, with diethylamino sulfur trifluoride. Finally, the phosphate was deprotected with trimethylbromosilane to provide 4-(fluoromethyl)phenyl phosphate. To attach a nucleoside or polynucleotide as R, for example, phosphate groups can be activated with standard reagents such as thionyl chloride or dicyclohexyl carbodiimide, and the resulting activated species reacted with hydroxyl groups on the corresponding molecule (e.g. the 3'-hydroxyl group of a nucleoside or polynucleotide to be attached to the phosphate group). These and similar reaction schemes employing conventional reagents and processes can be used to prepare suicide inhibitors of formula I.

The invention also provides methods for inhibiting phosphatase or phosphodiesterase enzymes utilizing suicide inhibitors of the formulas II and III

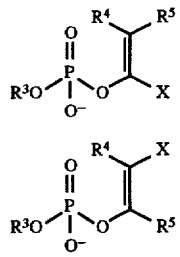

wherein

R³ is —H or a specificity element;

R⁴ and R⁵, which may be the same or may differ from one another, are each —H or an organic group having up to about 20 carbon atoms; and X is a leaving group.

As indicated in the above discussions there are a great number of known phosphatase and phosphodiesterase enzymes, and the naturally-occurring substrates for these enzymes are known. In accordance with the invention, the specificity elements employed will correspond to the specificity elements of these naturally-occurring substrates. Thus, generally speaking, the suicide inhibitors employed in the present invention will be constructed by incorporating the radical IV or V

into naturally-occurring substrates for the target enzymes.

As before, the leaving group X will be a group having sufficient leaving capacity to enable the inactivation of the target enzyme by covalent bonding within the active site of the enzyme. Suitable leaving groups include halogens (i.e. iodine, bromine, chlorine and fluorine) and acyl groups —COR² wherein R² is defined as above. Phenyl groups or $C_1$ to $C^{10}$ alkyl groups optionally substituted with phenyl are conveniently employed as R² and are thus preferred.

Representative organic groups R⁴ and R⁵ include aliphatic groups (e.g. alkyl), combined aliphatic-aromatic groups (e.g. benzyl), or aromatic groups (e.g. phenyl). Groups such as —H and lower alkyl are conveniently employed and therefore preferred for R⁴ and R⁵ in many instances.

Representative specificity elements, R³ will include aliphatic, aromatic, or combined aliphatic-aromatic groups, generally having up to about 50 carbon atoms and optionally containing halogen (especially fluorine), nitrogen, oxygen or sulfur groups. Included among these are straight or branched chain alkyl groups, phenyl groups, alkyl-phenyl groups, carbohydrate groups such as glucose or fructose groups, nucleosides, nucleotides, polynucleotides (generally having up to about 20 nucleotides), diacylglycerol and other lipid or glyceride derivatives.

R³ can thus be a group corresponding to a hydroxyl-containing amino acid, e.g. R³ can be —$CH_2$—C(H)($NH_3$)—$COO^-$ (corresponding to serine), —C(H)($CH_3$)—C(H)($NH_3^+$)—$COO^-$ (corresponding to threonine), or —Phenyl—p—$CH_2$—C(H)($NH_3^+$)—$COO^-$ (corresponding to tyrosine). In this manner, suicide substrates to serine or threonine phosphatases (e.g. Calcineurin, which has specificity for both) or to phosphotyrosine phosphatases (e.g. YOP 51, LAR, and CD45) are provided. In the case of Calcineurin, the suicide inhibitors can thus function as immunosuppressants, and in the case of phosphotyrosine phosphatases such as YOP 51, LAR and CD45 can function as cell growth regulators.

R³ can also be a nucleosides or nucleotide group, including ribonucleosides, deoxyribonucleosides, ribonucleotides and deoxyribonucleotides. In these cases suicide inhibitors can be provided to phosphodiesterases such as ribonucleases (RNases), e.g. RNase H (which is necessary for the viral life cycle of HIV), and RNase A or $T_1$ (which are used diagnostically in the sequencing of RNA). The invention thus provides suicide inhibitors of the formula IV or V wherein R³ is a group of the formula VI

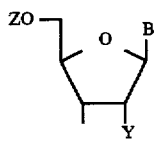   VI wherein

Z is —H, —PO$_3^=$, a nucleotide or a polynucleotide;
B is a purine or pyrimidine base; and
Y is —H or —OH.

In accordance with formula VI, nucleosides are provided where Z is —H, and nucleotides are provided where Z is —PO$_3^=$. Similarly, deoxyribonucleosides and deoxyribonucleotides are provided where Y is —H and ribonucleosides and ribonucleotides are provided where Y is —OH. Suitable purine or pyrimidine bases B include, for example, adenine, guanine, cytosine, uracil and thymine.

The invention further provides suicide inhibitors of phospholipid phosphatases such as phospholipase C, phospholipase D and phosphotitic acid phosphohydrolase (PA phosphohydrolase). Inhibitors of such phospholipid phosphatases are expected to have useful properties as antitumor agents. Suicide inhibitors of phospholipases C or D are thus provided where R$^3$ in formulas II and III is an inositol radical of formula VII (or a mono- or di-phosphate salt thereof) or a diacyl glycerol radical of formula VIII

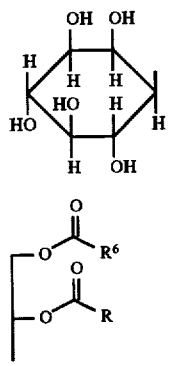  VII

VIII wherein in formula VIII the groups R$^6$ can be the same or can differ from one another and are fatty acid chains, usually containing an even number of carbon atoms up to a total of about 24, typically from 14 to 24 carbon atoms. Compounds wherein R$^3$ is a diacyl glycerol of formula VIII will also serve as suicide inhibitors of PA phosphohydrolase and thereby provide antitumor agents.

The invention also provides suicide inhibitors of carbohydrate phosphatases such as glucose-6-phosphatase and fructose-1,6-diphosphatase, which can be used to regulate glucose metabolism and gluconeogenesis and to control glucose levels. These inhibitors will have the formulas IX or X:

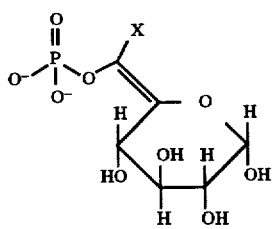  IX

-continued

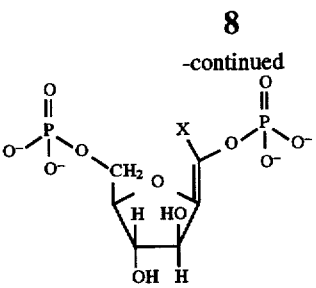  X

The invention also provides suicide inhibitors of cyclic adenosine monophosphate (c-AMP) and cyclic guanosine monophosphate (g-AMP) phosphodiesterases. These inhibitors have the formula XI

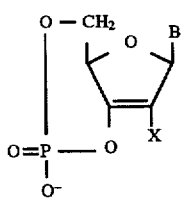  XI wherein B is adenine or guanine and X, R$^4$ and R$^5$ are as defined above in formulas II and III. Such inhibitors will be useful, for example, in relation to asthma, wherein other inhibitors of c-AMP and g-AMP phosphodiesterases are known to have therapeutic properties.

It will be understood that suicide inhibitors of the invention can also contain conventional radioactive or fluorescent labels which become covalently attached in the enzyme active site upon inhibition. Suicide inhibitors containing such labels can serve not only to map enzyme active sites, but also diagnostically in the quantitation of enzyme levels in patient samples to determine whether abnormalities exist. As previously indicated, phosphatase and phosphodiesterase enzymes are involved in numerous biological processes including those affecting cell growth and signal processing, and accordingly abnormal levels of these enzymes confer disorders to patients having them.

Another preferred embodiment of the invention provides a method for preparing an enol phosphate compound bearing a leaving group at the 1-position, comprising dehydrohalogenating a compound of formula XII

XII wherein X is halogen and Z is halogen or an acyl leaving group, and R$^3$, R$^4$ and R$^5$ are defined as above in formula II, i.e. R$^3$ is —H or a specificity element, and R$^4$ and R$^5$, which may be the same or may differ from one another, are —H or an organic group having up to about 20 carbon atoms, in the presence of a metal amide base so as to produce an enol phosphate compound of formula XIII

XIII wherein Z, R$^3$, R$^4$ and R$^5$ are as defined above.

Specific representative groups R$^3$, R$^4$ and R$^5$ are set forth in the discussions above with regard to compounds encompassed by formula II. Acyl groups Z will generally have the formula O—CO—R wherein R is usually an aliphatic, aromatic or combined aliphatic aromatic group, typically having from 1 to about 20 carbon atoms.

The particular metal amide employed in the invention is not critical and those ordinarily skilled in the art will be able to select and use suitable metal amides given the teachings herein. Generally, the metal amide will have the formula $MN(G_1)(G_2)$ wherein M is a metal and $G_1$ and $G_2$ are organic groups, e.g. alkyl groups containing up to about 10 carbon atoms and optionally substituted with phenyl, or triorganosilyl groups, e.g. trialkylsilyl groups wherein the alkyl group contains up to about 10 carbon atoms and is optionally substituted with phenyl. Preferably, the metal M will be an alkali metal or an alkaline earth metal, more preferably lithium, sodium or potassium.

Preferred reactions are conducted in an organic solvent with cooling, preferably at temperatures below about 0° C. It is also preferred to carry out the reactions in non-polar organic solvents, for example non-polar aromatic solvents such as benzene or alkylbenzene solvents (e.g. toluene). As shown in Table 1 (compound XVI), while similar results were obtained using lithium, sodium, or potassium bis(trimethylsilyl)amide (LiHMDS, NaHMDS, KHMDS) in toluene, performing the reaction in the more polar solvent, tetrahydrofuran (THF), led to reduced yields of the vinyl bromide.

In one desirable overall synthesis, compound XII above, wherein Z is a halogen (e.g. compound XV, Table 1), is obtained by halogenation of a compound of the formula XIV

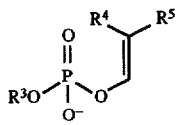

to provide a dihalo compound of formula XII wherein Z is halogen.

TABLE 1

| | Br Br<br>RO Br<br>XV | Base → | Br<br>RO<br>XXVIII | Br O<br>RO Br<br>XVI | Br<br>RO<br>XVII | Yield |
|---|---|---|---|---|---|---|
| | | DBU/THF | 39 | 38 | 23 | 86% |
| | | (Li, Na) KHMDS/ PhCH₃ | <1 | >99 | <1 | 91% |
| R = (OEt)₂P (O) | | LiHMDS/ THF | 1 | 96 | 3 | 86% |
| | | KHMDS/ THF | 3 | 91 | 6 | 65% |
| | | KHMDS/ PhCH₃/18-C-6 | 16 | 52 | 32 | 28% |

While the present invention is not limited by any theory, with regard to the dehydrohalogenation reaction, it is thought that the regioselectivity of the elimination reaction is controlled by precomplexation of the metal amide to the phosphate ester. If such complexation were to take place, the elimination of bromide from the 2-position via a 7-membered ring transition state might be preferred over elimination from the 1-position via an 8-membered ring transition state. The preference for a 7-membered ring structure has been demonstrated for the directed lithiation of alkyl amides.

The possibility that a complex-induced proximity effect may be an important element of these reactions is consistent with the solvent dependence displayed by the metal amide-mediated elimination reactions. A further test of this hypothesis was to determine the effect of added crown ethers on the regioselectivity of the reaction. Treatment of the dibromide XV (Table 1), with KHMDS in toluene (—78° C.) in the presence of 18-crown-6 led to the formation of a complex mixture. A large percentage of these products had undergone cleavage of the phosphate ester group. Significantly however, all three vinyl bromides were now formed in this reaction. The loss of selectivity that was induced by the presence of a crown ether supports that precoordination of the metal amide is a factor in this reaction.

The elimination reactions of the invention permit the synthesis of sensitive compounds that are not available by other means. For example, treatment of the iodide (XIX)

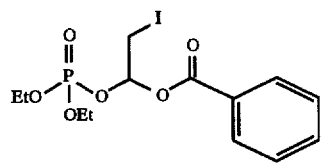

(available by treatment of diethyl vinyl phosphate with PhCOOAg/I₂) with the metal amide LiHMDS in toluene leads to the formation of the ketene acetal (XX) in 45% yield:

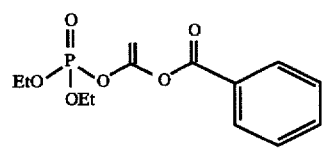

Presumably, in this case, the operation of a CIPE both suppresses unwanted side reactions, and facilitates the dehydrohalogenation reaction.

It will be noted from Table 1 that enol phosphate compounds bearing leaving groups at the 2-position (compound XVI) (e.g. suicide inhibitors of formula III above) are also available through dehydrohalogenation of compound XII wherein X is halogen, preferably in a polar solvent and in the presence of a base other than a metal amide (e.g. DBU).

In order to promote a further understanding of the invention and its features and advantages, the following specific Experimentals are provided. It will be understood that these Experimentals are illustrative, and not limiting, of the invention.

Experimental: Inhibition of Prostatic Acid Phosphatase

In this experimental, human prostatic acid phosphatase (PAP) was used as a model enzyme. Although PAP has a broad substrate specificity in-vitro, it displays a preference for aryl phosphates. This phosphatase is an important diagnostic marker for prostate cancer, and there is evidence that it may be involved in the regulation of androgen receptor activity in prostate cells.

The suicide inhibitor employed was 4-(fluoromethyl)phenyl phosphate, FMPP, an inhibitor of formula I. Treatment of purified PAP with FMPP resulted in rapid, time-dependent inactivation of the enzyme (FIG. 1, A–D). The inactivation process displayed saturation kinetics ($K_i$=150 mM) and competitive inhibitors of PAP, inorganic phosphate (FIG. 1C) and tartaric acid (data not shown) protect against inactivation. The $t_{1/2}$ for inactivation at saturating levels of FMPP was 35 seconds. Doubling or halving the PAP concentration did not change the rate of inactivation.

As a possible mechanism for the inactivation process, it is thought that hydrolysis of the phosphate ester bond ($k_1$) leads to the formation of a metastable phenol or phenoxide at the active site. This phenol can partition off the enzyme ($k_{off1}$), or may suffer the elimination of fluoride ion ($k_{elim}$) to give a quinone methide that inactivates the enzyme ($k_{alk}$), or be released into solution ($k_{off2}$).

Because PAP generates a quinone methide each time it turns over, the enzyme inactivation may occur by metabolic inactivation (release of an electrophile to solution followed by alkylation of the enzyme from solution). To test this possibility, we inactivated the enzyme with FMPP in the presence of nucleophilic scavenging agents. The rate of inactivation was not slowed by the nucleophiles dithiothreitol (5 mM, data not shown), sodium azide (1 mM, data not shown), or cysteine (20 mM) (FIG. 1D). Even the presence of 50 mM sodium azide did not stop the inactivation. These results suggested that inactivation of the enzyme takes place before the alkylating agent leaves the active site. If the reactive species had left the active site and then alkylated the enzyme at some distal but critical residue, it most likely would have been intercepted by the nucleophilic scavengers, with a consequent reduction in the enzyme inactivation rate.

The potency of the inactivation caused by suicide inhibitors such as FMPP is a function of two ratios, $k_{off1}:k_{elim}$, and $k_{off2}:k_{alk}$. If either ratio is large then inactivation is unlikely to occur, and vice versa. Aryl phosphates with poor leaving groups, such as the benzylic acetate XX, are expected to have slow relative rates of $k_{elim}$, and therefore to inactivate the enzyme slowly if at all. In fact, benzylic acetate XX, which is a substrate for PAP, was not as potent as FMPP. The time course of the PAP-catalyzed hydrolysis of benzylic acetate XX (monitored by $^1$H nuclear magnetic resonance spectroscopy) showed the rapid formation of an intermediate, presumably a corresponding dephosphorylated phenol which had a $t_{1/2}$ of about six hours and decomposed to a corresponding p-hydroxybenzyl alcohol, presumably through a quinone methide.

To test whether FMPP inactivated PAP by functioning as an affinity reagent, phosphonate XXI (FIG. 1B) was synthesized and assayed.

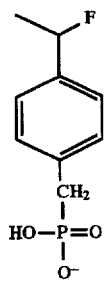

XXI

Although this phosphonate does not contain a scissile P—O bond and therefore cannot undergo enzyme-catalyzed hydrolysis, it bears a strong structural resemblance to FMPP and is a competitive inhibitor of PAP. Incubation of XXI with PAP resulted in virtually no time-dependent enzyme-inactivation, even after 20 minutes (FIG. 1B). This experiment suggests that PAP inactivation by FMPP requires cleavage of a P—O bond, and that the benzylic fluoride moiety of FMPP is not a sufficiently reactive electrophile to bring about alkylation of the enzyme.

FMPP appears to selectively inactivate phosphatases with a particular affinity for aryl phosphates; it does not, for example, inactivate alkaline phosphatase, which displays no specificity for aryl phosphates, even though FMPP is a substrate for the enzyme.

In further time-dependent inactivation studies, FMPP analogues wherein the fluorine was replaced by chlorine and bromine proved to inactivate the PAP enzyme. Additionally, a the chloro- analogue of FMMP wherein the phenyl group had a nitro group at the ortho position (to the phosphate), succesfully inactivated the PAP enzyme with substantially greater potency.

Experimental: Preparation and Use of Halo Enol Phosphates

A. General Synthetic Approach

The synthesis of compounds such as those of formula II was generally approached as follows: Bromination of diethyl vinyl phosphate afforded the dibromide XV (Table 1) in 99% yield. Treatment of the dibromide with lithium diisopropylamide in Et20 at −78° C. gave the desired vinyl bromide XVI as the sole organic soluble product.6 The best yields of the bromide XVI were obtained by performing the reaction in non-polar solvents such as toluene at −78° C. Similar results were obtained using lithium, sodium, or potassium bis(trimethylsilyl)amide (LiHMDS, NaHMDS, KHMDS) in toluene. Performing the reaction in THF led to reduced yields of the vinyl bromide (Table 1). The use of bases other than metal amides led largely to the formation of the 2-bromo isomers.

B. Specific Preparations

General Methods. All reactions were conducted in oven-dried (120° C.) or flame-dried glassware under an atmosphere of dry argon or nitrogen. All solvents were purified before use. Et$_2$O and THF were distilled from sodium benzophenone ketyl. Methylene chloride, toluene, and acetonitrile were distilled from CaH$_2$.

$^1$H NMR spectra were measured at 400 MHz on a Varian VNMR 400 instrument. Chemical shifts are reported in d units to 0.01 ppm precision with coupling constants reported in Hertz to 0.1 Hz precision. Residual chloroform (d 7.26 ppm) was used as an internal reference for spectra measured in CDCl$_3$. $^{13}$C NMR spectra were recorded at 100 MHz on a Varian VNMR 400 instrument. Chemical shifts were reported in d units to 0.1 ppm precision with coupling constants reported in Hertz to 1 Hz precision. Residual chloroform (d 77.0 ppm) was used as an internal reference for spectra measured in CDCl$_3$. $^{31}$P NMR spectra were recorded at 146 MHz on a Nicolet NT-360 instrument. Chemical shifts were reported in d units to 0.01 ppm precision ($^1$H decoupled). H$_3$PO$_4$ was used as an external reference for the $^{31}$P spectra.

Infrared spectra were recorded on a Perkin-Elmer Model 298 Infrared Spectrophotometer. High resolution mass spectra were measured at 70 eV on a Kratos GC/MS 80 RFA Mass Spectrometer at the Indiana University Mass Spectrometry Laboratory.

Analytical thin-layer chromatography (TLC) was performed by using 2.5 cm×10 cm Kieselgel 60 F$_{254}$ plates with a 0.25-mm thickness of silica gel. Compounds were visualized using anisaldehyde stain (93.67 mol % EtOH, 3.99 mol % H$_2$SO$_4$, 1.25 mol % anisaldehyde, 1.09 mol % AcOH). Flash chromatography was performed using Kieselgel 60 (230–400 mesh). Unless otherwise noted, all compounds purified by chromatography were sufficiently pure (>95% by $^1$H NMR analysis) for use in subsequent reactions.

Diethyl Vinyl Phosphate A solution of n-butyllithium (2.50M solution in hexane, 147.0 ml, 0.368 mol) in THF (294 ml) was stirred for 30 min. at 0° C., followed by an additional 16 hours at 25° C. This solution was then added dropwise to a solution of diethyl chlorophospate (79.6 ml, 0.551 mol) in THF (100 ml) at −78° C. After the addition, the reaction mixture was warmed to 25° C. over 45 min. and then concentrated in vacuo. The resulting oil was diluted with $CH_2Cl_2$ (1000 ml) and washed with 10% aqueous sodium phosphate buffer (pH=7) (6×100 ml), dried ($MgSO_4$), and concentrated in vacuo. Flash chromatography (20% hexanes/$Et_2O$) afforded the title compound (61.10 g, 92.3% yield) as a clear, tan oil. $^1H$ NMR, $^{31}P$ NMR, and MS spectra for diethyl vinyl phosphate were consistent with the data reported in the literature: $^1H$ NMR ($CDCl_3$, 400 MHz) d 6.54 (td, 1 H, J=13.4 Hz, $C^{1-}$ and $C^{2a}$-H; J=6.5 Hz, $C^1$-H and P; J=5.9 Hz, $C^1$l and $C^{2b}$-H), 4.88 (td, 1 H, J=13.4 Hz, $C^{2a}$- anti $C^1$-H; J=1.9 Hz, $C^{2a}$- and $C^{2b}$-H; J=1.1 Hz, $C^{2a}$-H and P), 4.53 (td, 1 H, J=5.9 Hz, $C^{2b}$- and $C^1$-H; J=2.7 Hz, $C^{2b}$-H and P; J=1.9 Hz, $C^{2b}$- and $C^{2a}$-H), 4.13 (m, 4 H), 1.32 (dt, 6 H, J=7.2 Hz, $C^4$- and $C^3$-H; J=1.1 Hz, $C^4$-H and P); $^{13}C$ NMR ($CDCl_3$, 100 MHz) d 142.9 (d, J=6 Hz), 100.2 (d, J=11 Hz), 64.6 (d, J=6 Hz), 16.0 (d, J=7 Hz); $^{31}P$ NMR ($H_3PO_4$, 146 MHz) d −4.22; IR (neat) 2995, 2940, 2920, 1645, 1395, 1375, 1320, 1280, 1135, 1100, 1015 (broad), 875, 820; LRMS, m/e (relative intensity) 181.1 (28.1), 153.0 (51.6), 125.0 (58.7), 109.0 (100.0), 99.0 (87.9), 91.0 (34.0), 81.0 (99.3); HRMS for $C_6H_{13}O_4P$ [M+H$^+$], calcd. 181.0630; found, 181.0612.

Diethyl 1,2-Dibromoethyl Phosphate. A solution of diethyl vinyl phosphate (5.00 g, 27.8 mmol) in $CH_2Cl_2$ (500 ml) at 0° C. was treated with $Br_2$ (1.43 ml, 27.8 mmol) until the orange color persisted for 15 min. The reaction mixture was warmed to 25° C. over 30 min., diluted with $Et_2O$ (1000 ml), washed with 5% aqueous $NaHSO_3$ (2×75 ml), dried ($MgSO_4$), and concentrated in vacuo. Flash chromatography (5% $Et_2O/CH_2Cl_2$) afforded the title compound (9.36 g, 99.2% yield) as a clear, colorless oil: $^1H$ NMR ($CDCl_3$, 400 MHz) d 6.44 (td 1 H J=9.4 Hz, $C^1$- and $C^{2a}$-H; J=7.8 Hz, $C^1$-H and P; J=3.5 Hz, $C^1$- and $C^{2a'}$-H), 4.23 (m, 4 H), 3.93 (dd, 1 H, J=11.0 Hz, $C^{2a}$- and $C^{2a'}$-H; J=9.4 Hz, $C^{2a}$- and $C^1$-H), 3.87 (td, 1 H, J=11.0 Hz, $C^{2a'}$- and $C^{2a}$-H; J=3.5 Hz, $C^{2a'}$- and $C^1$-H; J=3.0 Hz, $C^{2a'}$-H and P), 1.39 (dt, 6 H, J=7.0 Hz, $C^4$- and $C^3$-H; J=1.1 Hz, $C^4$-H and P); $^{13}C$ NMR ($CDCl_3$, 100 MHz) d 76.2 (d, J=6 Hz), 65.3 (d, J=6 Hz), 35.3 (d, J=10 Hz), 16.1 (d, J=5 Hz), 16.0 (d, J=5 Hz); $^{31}P$ NMR ($H_3PO_4$, 146 MHz) d −3.32; IR (neat) 3000, 2945, 2920, 1395, 1375, 1285, 1160, 1115, 1010 (broad), 920, 795, 685; LRMS, m/e (relative intensity) 342.9 (73.6), 340.9 (100.0), 338.9 (74.8), 261.0 (86.4), 259.0 (86.8), 181.2 (29.3), 155.1 (42.5), 109.1 (55.5); HRMS for $C_6H_{13}O_4PBr_2$ [M+H$^+$], calcd. 338.8996; found, 338.8843.

Diethyl Z-2-Bromovinyl Phosphate (XVIII) and Diethyl E-2-Bromovinyl Phosphate (XVII).[4] DBU (22.0/1, 0.147 mmol) was added dropwise to a solution of diethyl 1,2-dibromotheyl phosphate (25.0 mg, 73.5/mol) in THF (500/1) at −30° C. and allowed to stir for 2 hours. The reaction mixture was warmed to 25° C. over 1 hour, diluted with $Et_2O$ (25 ml), washed with saturated aqueous $NaHSO_4$ (3×5 ml), 10% aqueous sodium phosphate buffer (pH=7) (1×5 ml), dried ($MgSO_4$), and concentrated in vacuo. Flash chromatography (5% $Et_2O/CH_2Cl_2$) afforded the Z-2-bromide (XVIII) (6.4 mg, 34% yield) and a 62:38 mixture of the other vinyl bromides (geminal bromide (XVI); E-2-bromide (XVII)) (9.9 mg, 52% yield) as clear, colorless oils. $^1H$ NMR and $^{31}P$ NMR spectra for diethyl Z-2-bromovinyl phosphate and diethyl E-2-bromovinyl phosphate were consistent with the data reported in the literature[2]: (Z-2-bromide) $^1H$ NMR ($CDCl_3$, 400 MHz) d 7.08 (dd, 1 H, J=5.1 Hz, $C^1$-H and P; J=4.0 Hz, $C^1$- and $C^2$-H), 5.64 (dd, 1 H, J=4.03 Hz $C^2$-and $C^1$-H; J=1.9 Hz and P) 4.21 (m, 4 H), 1.37 (dt, 6 H, J=7.0 Hz, $C^4$- and $C^3$-H; J=1.1 Hz, $C^4$-H and P); $^{13}C$ NMR ($CDCl_3$, 100 MHz) d 139.4 (d, J=4 Hz), 92.5 (d, J=12 Hz), 65.3 (d, J=6 Hz), 16.1 (d, J=6 Hz); $^{31}P$ NMR ($H_3PO_4$, 146 MHz) d −3.75; IR (neat) 3000, 2950, 2925, 1645, 1395, 1375, 1285, 1220, 1165, 1025 (broad), 895, 810, 760, 670; LRMS, m/e (relative intensity) 261.0 (100.0), 259.0 (97.8), 179.0 (84.2), 155.0 (12.4), 123.0 (79.1), 109.0 (26.5), 91.0 (9.8), 81.0 (24.2); HRMS for $C_6H_{12}O_4PBr$ [M+H$^{30}$], calcd. 258.9735; found, 258.9732; (E-2-bromide) $^1H$ NMR ($CDCl_3$, 400 MHz) d 6.87 (dd, 1 H, J=11.6 Hz, $C^1$- and $C^2$-H; J=7.3 Hz, $C^1$-H and P), 6.09 (dd, J=11.6 Hz, $C^2$- and $C^1$-H;, J=1.5 Hz, $C^2$-H and P), 4.17 (m, 4 H), 1.35 (dt, 6 H, J=7.0 Hz, $C^4$- and $C^3$-H; J=1.1 Hz, $C^4$-H and P); $^{13}C$ NMR ($CDCl_3$, 100 MHz) d 140.9 (d, J=6 Hz), 96.3 (d, J=12 Hz), 65.2 (d, J=6 Hz), 16.1 (d, J=6 Hz); $^{31}P$ NMR ($H_3PO_4$, 146 MHz) d −4.69.

Diethyl 1-Bromovinyl Phosphate (XVI). Lithium bis(trimethylsilyl)amide (1.0M solution in hexanes, 0.162 ml, 0.162 mmol) was added dropwise to a solution of the dibromide (XV) (50.0 mg, 0.147 mmol) in toluene (6.0 ml) at −78° C. After the addition, the reaction mixture was warmed to 25° C. over 30 min., diluted with $Et_2O$ (25 ml), washed with saturated aqueous $NaHSO_4$ (3×5 ml), 10% aqueous sodium phosphate buffer (pH=7) (1×5 ml), dried ($MgSO_4$), and concentrated in vacuo. Flash chromatography (5% $Et_2O/CH_2Cl_2$) afforded the geminal bromide (XVI) (35.2 mg, 92.4% yield) as a clear, colorless oil: $^1H$ NMR ($CDCl_3$, 400 MHz) d 5.45 (dd, 1 H, J=3.2 Hz, $C^{2b}$- and $C^{2a}$-H; J=3.2 Hz, $C^{2b}$-H and P), 5.06 (dd, 1 H, J=3.2 Hz, $C^{2a}$- and $C^{2b}$-H; J=2.6 Hz, $C^{2a}$-H and P), 4.21 (m, 4 H), 1.37 (dt, 6 H, J=7.2 Hz $C^4$- and $C^3$-H; J=1.2 Hz, $C^4$-H and P); $^{13}C$ NMR ($CDCl_3$, 100 MHz) d 129.7 (d, J=11 Hz), 106.1 (d, J=6 Hz), 65.6 (d, J=6 Hz), 16.0 (d, J=6 Hz); $^{31}P$ NMR ($H_3PO_4$, 146 MHz) d −6.01; IR (neat) 2995, 2945, 2920, 1630, 1395, 1375 1290, 1150, 1100, 1020 (broad), 860, 815; LRMS, m/e (relative intensity) 261.0 (66.8), 259.0 (67.2), 21.7.0 (52.9), 189.0 (27.5), 161.0 (25.4), 137.1 (37.3), 109.0 (100.0), 91.0 (28.2), 81.0 (77.7), 69.0 (79.6); HRMS for $C_6H_{12}O_4PBr$ [M+H$^+$], calcd. 258.9735; found, 258.9741.

Diethyl 1-Benzoyloxy-2-Iodoethyl Phosphate (XIX). Diethyl 1-benzoyloxy-2-iodoethyl phosphate was synthesized by a method similar to that reported by Halperin and co-workers.[8] A solution of diethyl vinyl phosphate (0.500 g, 2.78 mmol) and silver benzoate (0.636 g, 2.78 mmol) in $Et_2O$ (2.5 ml) at 25° C. was treated with $I_2$ (0.705 g, 2.78 mmol) until the violet color persisted for 15 min. The reaction mixture was then filtered and washed with $Et_2O$ (50 ml). The organic layer was washed with 10% aqueous $Na_2CO_3$/1% $Na_2S_2O_3$ solution (2×5 ml), $H_2O$ (2×5 ml), saturated NaCl (1×5 ml), dried ($MgSO_4$), and concentrated in vacuo. Flash chromatography (5% $Et_2O/CH_2Cl_2$) afforded the iodobenzoate XIX (0.633 g, 53.3% yield) as a clear, colorless oil: $^1H$ NMR ($CDCl_3$, 400 MHz) d 8.10 (d, 2 H, J=7.5 Hz, $C^7$- and $C^8$-H), 7.62 (t, 1 H, J=7.5 Hz, $C^9$- and $C^8$-H, $C^9$- and $C^7$-H), 7.48 (t, 2 H, J=7.5 Hz, $C^8$- and $C^7$-H, $C^8$-and $C^9$-H), 6.55 (td, 1 H, J=7.3 Hz, $C^1$-H and P; J=4.8 Hz, $C^1$- and $C^{2a}$-H; J=4.3 Hz, $C^1$- and $C^{2a'}$-H), 4.17 (m, 4 H), 3.60 (td, 1 H, J=11.0 Hz, $C^{2a}$- and $C^{2a'}$-H; J=4.8 Hz, $C^{2a}$- and $C^1$-H, J=1.0 Hz and P) 3.57 (td, 1 H, J=11.0 Hz, $C^{2a'}$- and $C^{2a}$-H; J=4.3 Hz, $C^{2a'}$- and $C^1$-H; J=1.0 Hz, $C^{2a'}$-H and P), 1.31 (dt, 3 H, J=7.0 Hz $C^4$- and $C^3$-H; J=1.1 Hz, $C^4$-H and P), 1.30 (dt, 3 H, J=7.0 Hz, $C^4$- and $C^3$-H; J=1.1 Hz, $C^4$-H and P); $^{13}C$ NMR ($CDCl_3$, 100 MHz) d 164.9, 134.7, 130.9, 129.3, 91.4 (d, J=3 Hz), 65.0 (d, J=6 Hz), 64.9 (d, J=6 Hz), 16.1 (d, J=7 Hz), 4.3. (d, J=7 Hz); $^{31}$P NMR ($H_3PO_4$, 146 MHz) d -3.87; IR (NaCl solution cell, $CDCl_3$) 2988, 2936, 2913, 1265, 1171, 1119, 1034, 968, 959, 920, 716; LRMS, m/e (relative intensity) 429.0 (0.2), 307.0 (4.7), 259.1 (12.0), 179.0 (8.3), 123.0 (15.8), 106.0 (9.2), 105.0 (100.0), 85.9 (16.7), 83.9 (33.2), 77.0 (11.2); HRMS for $C_{13}H_{18}O_6PI$ [M+H$^+$], calcd. 428.9886; found, 428.9969.

Diethyl 1-Benzoyloxyvinyl Phosphate (XX). Lithium bis (trimethylsilyl)amide (1.0M solution in hexanes, 1.752 ml, 1.752 mmol) was added dropwise to a solution of the iodobenzoate XIX (0.250 g, 0.584 mmol) in toluene (50 ml) at -78° C. and allowed to stir for 30 min. The reaction mixture was then diluted with $Et_2O$ (150 ml), washed with saturated aqueous $NaHSO_4$ (3×25 ml), 10% aqueous sodium phosphate buffer (pH=7) (1×25 ml), dried ($MgSO_4$), and concentrated in vacuo. Flash chromatography (5% $Et_2O$/$CH_2Cl_2$) afforded the geminal benzoate XX (78.6 mg, 44.8% yield) as a clear, colorless oil: $^1$H NMR ($CDCl_3$, 400 MHz) d 8.10 (d, 2 H, J=7.5 Hz, $C^7$- and $C^8$-H), 7.63 (t, 1 H, J=7.5 Hz, $C^9$- and $C^8$-H, $C^9$- and $C^7$-H), 7.48 (t, 2 H, J=7.5 Hz, $C^8$- and $C^7$-H, $C^8$- and $C^9$-H), 4.78 (dd, 1 H, J=3.5 Hz, $C^{2b}$- and $C^{2a}$-H; J=2.2 Hz, $C^{2b}$-H and P), 4.54 (dd, 1 H, J=3.5 Hz, $C^{2a}$- and $C^{2b}$-H; J=1.1 Hz, $C^{2a}$-H and P), 4.23 (m, 4 H), 1.34 (dt, 6 H, J=7.0 Hz, $C^{4-}$ and $C^3$-H; J=1.1 Hz, $C^4$-H and P); $^{13}$C NMR ($CDCl_3$, 100 MHz) d 164.0, 149.3 (d, J=5 Hz), 134.9, 131.1, 129.4, 128.9, 86.1 (d, J=3 Hz), 65.4 (d, J=6 Hz), 16.1 (d, J=7 Hz); $^{31}$P NMR ($H_3PO_4$, 146 MHz) d -7.19; IR (NaCl solution cell, $CDCl_3$) 2988, 2932, 1752, 1672, 1277, 1204, 1177, 1063, 1034, 999, 916, 706; LRMS, m/e (relative intensity) 301.1 (15.8), 259.0 (55.9), 155.0 (6.7), 106.0 (22.1), 105.0 (100.0), 81.0 (7.3), 77.0 (37.7), 51.0 (10.3); HRMS for $C_{13}H_{17}O_6P$ [M+H$^+$], calcd. 301.0763; found, 301.0843.

C. Inactivation of Enzyme

The geminal bromide (XVI) was used in time-dependent inactivation testing. In a fashion similar to that set out for FIG. 1, the geminal bromide was incubated with YOP 51, and the results demonstrated the succesful inactivation of the enzyme.

While the invention has been illustrated and described in detail in the foregoing description, the same is to be considered as illustrative and not restrictive in character, it being understood that only the preferred embodiments have been described and that all changes and modifications that come within the spirit of the invention are desired to be protected.

What is claimed is:

1. A process for inhibiting a phosphatase or phosphodiesterase enzyme, comprising contacting the enzyme with a substrate for the enzyme which has the formula:

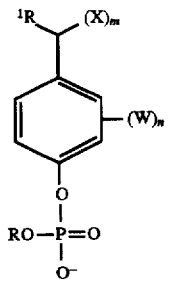

wherein:

X is a leaving group;

W is an alkyl or electron withdrawing group;

n is 0 to 4;

m is 1 to 3; and

R is —H, or a nucleoside or polynucleotide attached at the 3' or 5' position, with the proviso that when R is —H then R$^1$ is —H or a specificity element, and when R is a nucleoside or polynucleotide then R$^1$ is —H or an organic group having up to about 2 carbon atoms.

2. The process of claim 1 wherein R is —H and R$^1$ is —H or a specificity element.

3. The process of claim 1 wherein R is a nucleoside or polynucleotide and R$^1$ is an organic group having up to about 20 carbon atoms.

4. The process of claim 2 wherein R$^1$ is —H.

5. The process of claim 2 wherein R$^1$ is specificity element.

6. The process of claim 4 wherein m is 1 and X is a halogen.

7. The process of claim 6 wherein n is 0.

8. The process of claim 7 wherein X is fluoro.

9. A suicide inhibitor for a phosphatase or phosphodiesterase enzyme, comprising a substrate for the enzyme which has the formula:

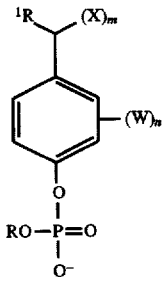

wherein:

X is a leaving group;

W is an alkyl or electron withdrawing group;

n is 0 to 4;

m is 1 to 3; and

R is —H, or a nucleoside or polynucleotide attached at the 3' or 5' position, with the proviso that when R is —H then R$^1$ is —H or a specificity element, and when R is a nucleoside or polynucleotide then R$^1$ is —H or an organic group having up to about 20 carbon atoms.

10. The suicide inhibitor of claim 9 wherein R is —H and R$^1$ is —H or a specificity element.

11. The suicide inhibitor of claim 9 wherein R is nucleoside or polynucleotide and R$^1$ is an organic group having up to about 20 carbon atoms.

12. The suicide inhibitor of claim 10 wherein R$^1$ is —H.

13. The suicide inhibitor of claim 10 wherein R$^1$ is a specificity element.

14. The suicide inhibitor of claim 12 wherein m is 1 and X is a halogen.

15. The suicide inhibitor of claim 14 wherein n is 0 and X is fluoro.

16. The suicide inhibitor of claim 9, wherein R is a nucleoside and R1 is —H.

17. The suicide inhibitor of claim 9, which is a suicide inhibitor for a phosphatase or phosphodiesterase enzyme selected from the group consisting of prostatic acid phosphatase, phospholipase C, phospholipase D, PA phosphohydrolase, phosphoserine/threonine phosphatase, glucose-6-phosphatase, ribonuclease A, and phosphotyrosine phosphatase.

18. The suicide inhibitor of claim 11 wherein R1 is an aliphatic, aromatic, or combined aliphatic-aromatic group, optionally containing one or more halogen, sulfur, oxygen or nitrogen atoms.

* * * * *

UNITED STATES PATENT AND TRADEMARK OFFICE
CERTIFICATE OF CORRECTION

PATENT NO : 5,714,361

DATED : February 3, 1998

INVENTOR : Theodore S. Widlanski

It is certified that error appears in the above-identified patent and that said Letters Patent is hereby corrected as shown below:

In col. 13, line 17, please delete "$C^11$" and insert in lieu thereof —$C^1$-—.

In col. 13, line 18, please delete "anti" and insert in lieu thereof —and—.

In col. 14, line 4, please insert —, $C^1$-H— immediately after "Hz".

In col. 14, line 12, please delete "$[M+H^{30}]$" and insert in lieu thereof —$[M+H^+]$—.

In col. 14, line 40, please delete "21.7.0" and insert in lieu thereof —217.0—.

In col. 14, line 63, please insert —, $C^{2a}$-H- between "J=1.0 Hz" and "and P)".

In col. 16, line 5, please delete "2" and insert in lieu there —20—.

In col. 16, line 44, please insert —a— immediately after "is".

Signed and Sealed this

Twenty-fifth Day of January, 2000

Attest:

Attesting Officer

*Acting Commissioner of Patents and Trademarks*